(12) United States Patent
Wooh

(10) Patent No.: US 6,253,618 B1
(45) Date of Patent: Jul. 3, 2001

(54) APPARATUS AND METHOD FOR SYNTHETIC PHASE TUNING OF ACOUSTIC GUIDED WAVES

(75) Inventor: Shi-Chang Wooh, Bedford, MA (US)

(73) Assignee: Massachusetts Intitute of Technology, Cambridge, MA (US)

( * ) Notice: Subject to any disclaimer, the term of this patent is extended or adjusted under 35 U.S.C. 154(b) by 0 days.

(21) Appl. No.: 09/644,376

(22) Filed: Aug. 23, 2000

Related U.S. Application Data
(60) Provisional application No. 60/169,826, filed on Dec. 8, 1999.

(51) Int. Cl.[7] .............................. G01N 29/06; A61B 8/14; A61B 8/00
(52) U.S. Cl. ................................................ 73/602; 73/626
(58) Field of Search .......................... 73/602, 625, 626, 73/627, 628, 641; 600/443, 447

(56) References Cited

U.S. PATENT DOCUMENTS

| | | | |
|---|---|---|---|
| 4,127,035 | 11/1978 | Vasile | 73/629 |
| 4,248,092 | 2/1981 | Vasile et al. | 73/643 |
| 4,437,031 | 3/1984 | Gunshor et al. | 310/313 B |
| 4,482,822 * | 11/1984 | Kubota et al. | 73/625 |
| 4,688,429 | 8/1987 | Holroyd | 73/602 |
| 5,129,262 | 7/1992 | White et al. | 73/599 |
| 5,154,081 | 10/1992 | Thompson et al. | 73/597 |
| 5,172,343 * | 12/1992 | O'Donnell | 367/7 |
| 5,212,988 | 5/1993 | White et al. | 73/599 |
| 5,763,785 * | 6/1998 | Chiang | 73/609 |
| 5,767,410 | 6/1998 | Lareau et al. | 73/623 |
| 5,827,188 * | 10/1998 | Wright et al. | 600/447 |

FOREIGN PATENT DOCUMENTS

| | | | |
|---|---|---|---|
| 0 935 258 A1 | 8/1999 | (EP) . | |
| 2008756 | 7/1982 | (GB) . | |
| 2164220 | 2/1988 | (GB) . | |
| 4-64350 * | 2/1992 | (JP) | 600/447 |
| WO 96/22527 | 7/1996 | (WO) . | |

* cited by examiner

Primary Examiner—Hezron Williams
Assistant Examiner—Rose M. Miller
(74) Attorney, Agent, or Firm—Iandiorio & Teska

(57) ABSTRACT

A synthetic phase tuned multi-mode acoustic guided wave system and method activates at least one of a plurality of elements as a receiver or a transmitter and at least two of the elements as transmitters or receivers, respectively, and sequentially excites each of the transmitter elements for creating a train of acoustic guided waves which includes a selected mode, and shifts the acoustic guided waves of the selected mode sensed by the receivers by a period which is a function of the phase velocity of the selected mode and sums them to reinforce the selected mode.

6 Claims, 5 Drawing Sheets

APPARATUS AND METHOD FOR SYNTHETIC PHASE TUNING OF ACOUSTIC GUIDED WAVES

RELATED APPLICATIONS

The application claims the benefit of U.S. Provisional Patent Application No. 60/169,826, filed Dec. 8, 1999.

FIELD OF INVENTION

This invention relates generally to a nondestructive evaluation apparatus and method, and more particularly to an apparatus and method for synthetically tuning multi-mode waves to a singular wave mode.

BACKGROUND OF INVENTION

Acoustic Guided waves, such as Lamb waves, are typically used to carry out ultrasonic nondestructive evaluation (NDE) of thin-wall structures such as pipes, shells, membranes, and plates. Guided waves are preferred to bulk waves because they can travel long distances, thereby making it possible to inspect wide areas with fewer measurements. Guided waves are generally analyzed by the well-known Rayleigh-Lamb wave dispersion relationship, expressed in terms of the thickness of the material and certain material constants, such as the modulus of elasticity, Poisson's ratio, or wave velocities. In determining dispersion equations, a set of curves can be obtained which relates phase velocities and frequencies. Such a set of curves is shown in FIG. 1, which is graph of the multiple dispersion curves corresponding to propagation modes for waves in an aluminum plate of a thickness $2h$.

Guided waves are both multi-modal and dispersive in nature. They are dispersive, meaning that waves oscillating in different frequencies travel at different speeds. In other words, phase velocity is not a constant value but a function of frequency. This means that the wave motion depends on the characteristics of the excitation signal. As a result, a broadband signal such as a spike pulse traveling in a dispersive medium may significantly change its shape as it propagates in the medium. On the other hand, the shape of an extremely narrowband signal, such as a tone burst signal, is preserved as it propagates in the medium.

Since broadband pulses are often too complicated and difficult to analyze, a more conventional approach is to use narrowband signals whose carrier frequency is swept over the width of the frequency band of interest. The advantage to this approach is that the signal retains its shape as it propagates in the medium. It is thus easier to analyze data and visualize the propagating and reflecting waves directly in the time domain.

In addition to dispersion, the other characteristic that distinguishes guided waves from bulk ultrasonic waves is their multi-modality. For a given thickness and frequency, there may exist many different propagation modes which are basically grouped into two different fundamental families: symmetric (S) and anti-symmetric (A) mode, such as those shown in FIG. 1. The Rayleigh-Lamb relationship yields infinitely many harmonic solutions for each mode. But, for NDE, it is desirable to differentiate one particular mode of propagation from the other modes, resulting in fewer peaks in the waveforms acquired.

Each dispersion curve corresponds to a particular mode of propagation and, for any given frequency, there exists at least two modes of propagation. These signals in their untuned state are generally too complicated to analyze and therefore it is necessary to distinguish a particular mode of interest from the other co-existing modes. Two common systems for generating guided waves in a selected mode are angle wedge tuners and array transducers. These systems are described separately below.

The most common system for generating guided waves is an angle wedge tuner or oblique angle insonification system. In general, a variable or fixed angle wedge transducer is used for controlling the incident angle of the applied signal. The wedge may be placed directly on the specimen, or alternatively, the insonification and detection can be made without direct contact using immersion and air-coupled transducers.

The basic principle for wedge tuning is Snell's law:

$$\sin\theta_w = \frac{c_w}{c_p} \tag{1}$$

where $\theta_w$ is the angle of incidence for tuning a selected mode propagating at the phase velocity $c_p$, and $c_w$ is the longitudinal wave velocity in the wedge which typically is 2,720 m/s. Accordingly, once the carrier frequency of the tone burst signal, the thickness of the medium under test and the longitudinal wave velocity in the wedge are known, the graph of FIG. 1 may be used to determine the required incident angle to tune the signal to the selected mode.

Problems associated with the angle wedge transducer include the difficulty of accurately setting the angle of incidence, since the variable wedge is manipulated manually. Accordingly, the sensitivity due to misalignment is uncertain and error levels may vary for different modes and frequencies. Another drawback results from the numerous interfaces that the signal must traverse in the wedge assembly. Typically, a variable angle wedge transducer includes two parts, a main wedge and block rotating around the wedge. Since the transducer is mounted on the block, three interfaces exist in the transducer-wedge assembly: one between the transducer and the rotating block; one between the rotating block and the main wedge; and one between the wedge and the medium under test. These interfaces can introduce reflections, resulting in unwanted peaks in the transmitted signal. This problem is greater for smaller angles of incidence, where small multiple reflections may occur. Another limitation of the wedge tuning technique is that Snell's Law becomes invalid in cases where $c_p$ is less than $c_w$. Consequently, angle wedge transducers cannot tune modes whose phase velocity falls below that of the longitudinal waves in the wedge. For example, the $A_0$ mode in the low frequency range cannot be tuned using an angle wedge tuner, because $c_p$ is less than 2,720 m/s as shown in FIG. 1. Yet another disadvantage in the angle wedge transducer comes from the fact that the wedge works as a delay block as a whole, requiring additional travel time that must be taken into account in the analysis of the received signal. Furthermore, the signal may be attenuated significantly before impinging the medium under test.

Another commonly used method for nondestructive evaluation involves the use of array transducers for single mode excitation of Lamb waves. One type of array transducer is a comb transducer. Another type of array transducer is an interdigital transducer. These devices are able to tune a desired mode by matching the transducer element spacing with a frequency of the excitation signal. Both of these array transducers are linear arrays having elements that are placed at a certain distance apart. A gated sinusoidal signal excites all the elements at the same time. By adjusting the distance between the elements, it is possible to generate guided waves of a wavelength equal to the distance between the elements.

Although array transducers can be more effective than the angle wedge transducer, there are disadvantages to using array transducers. The most critical problem is that the wave inherently propagates bidirectionally. This is because all of the transducer elements are simultaneously activated by the same signal, resulting in a symmetric excitation pattern. As a consequence, waves emanate from both sides of the transducer elements. Another disadvantage is that the transducer arrays cannot be effectively used as receivers because they are not able to accommodate the time delays introduced during reception.

SUMMARY OF THE INVENTION

It is therefore an object of this invention to provide an apparatus and method for synthetically tuning multi-mode waves to a single wave mode.

It is a further object of this invention to provide such an apparatus and method that utilizes standard transmission and receiving devices.

It is a further object of this invention to provide such an apparatus and method that enables a received wave to be tuned to any one of a number of wave modes.

It is a further object of this invention to provide such an apparatus and method in which the received waves can be stored for later processing or processed in real time to tune the received waves to the desired wave mode.

The invention results from the realization that a truly effective nondestructive evaluation system and method can be obtained by transmitting a multi-mode wave from each of a plurality of transmitters, receiving the plurality of transmitted waves with a receiver, shifting the received waves by an amount which reinforces a selected wave mode and summing the received, shifted waves to obtain a wave which is synthetically tuned to the selected wave mode.

This invention features a synthetic phase tuned multi-mode acoustic guided wave system including a plurality of spaced transducer elements. The invention further includes a switching device for activating at least one of the elements as a receiver or a transmitter and at least two of the elements as transmitters or receivers, respectively. Also included is a control device for sequentially exciting each of the transmitter elements for creating a train of acoustic guided waves which includes a selected mode, and for shifting the acoustic guided waves of the selected mode sensed by the receivers by a period which is a function of the phase velocity of the selected mode and summing them to reinforce the selected mode. In preferred embodiments there may be activated one transmitter and a plurality of receivers or one receiver and a plurality of transmitters.

This invention also features a method for a synthetic phase tuning of acoustic guided waves including activating at least one of a plurality of elements as a receiver or transmitter and at least two of the elements as transmitters or receivers, respectively; and sequentially exciting each of the transmitter elements for creating a train of acoustic guided waves which includes a selected mode and shifting the acoustic guided waves of the selected mode sensed by the receivers by a period which is a function of the phase velocity of the selected mode and summing them to reinforce the selected mode. In preferred embodiments there may be activated one transmitter and a plurality of receivers or one receiver and a plurality of transmitters.

BRIEF DESCRIPTION OF THE DRAWINGS

Other objects, features and advantages will occur to those skilled in the art from the following description of a preferred embodiment and the accompanying drawings, in which.

DETAILED DESCRIPTION

Figure 2:
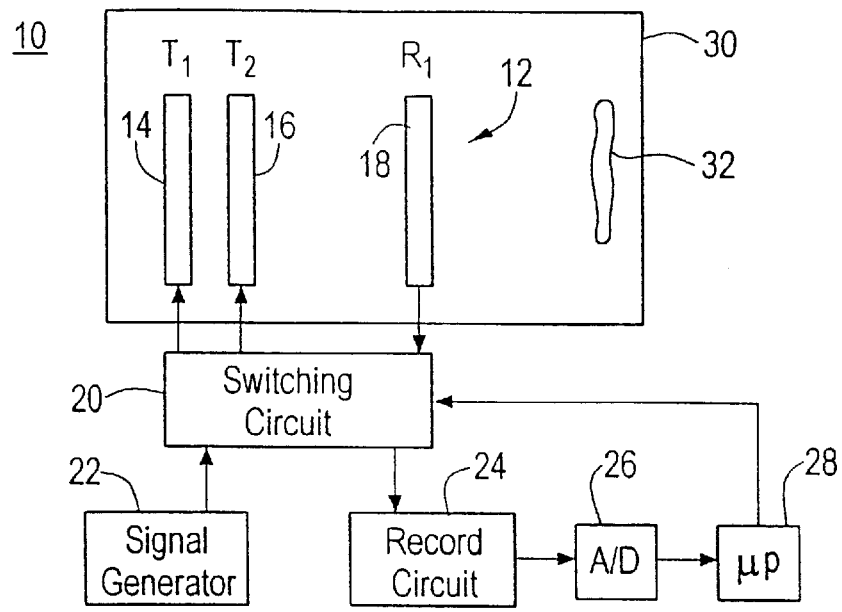
FIG. 2 is a schematic block diagram of a synthetic phase tuned multimode acoustic wave system according to the present invention.

There is shown in FIG. 2 a synthetic phase tuned multi-mode acoustic guided wave system 10 according to this invention which includes a multi-element array 12 of spaced elements 14, 16, 18, a switching circuit 20 and a signal generator 22 for driving the elements which are operated as transmitters. There is also a record circuit 24 for receiving the waves from the receivers which are then converted from analog to digital form by A to D converter 26 and time shifted and summed in microprocessor 28 so that the desired selected mode is reinforced in contrast to the other modes and noise.

In operation, in FIG. 2 elements 14 and 16 are operated independently as transmitters, element 18 is operated as a receiver. Switching circuit 20, which typically is controlled by microprocessor 28, provides a tone burst signal from signal generator 22 to elements 14 and 16 acting as transmitters. In the pulse echo mode, the individual waves from elements 14 and 16 enter a medium 30 containing for example a flaw 32. The signals received from elements 14 and 16 acting as transmitters is received by element 18 acting as a receiver and the return signal is delivered by switching circuit 20 to recording circuit 24. Here after suitable signal processing and amplification the signals are delivered to A to D converter 26 and into microprocessor 28 where they are time shifted and summed to provide the reinforced tuned synthetic wave.

Figure 3:
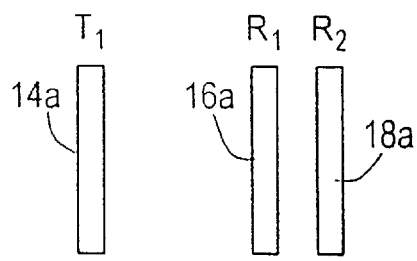
FIGS. 3, 4, 5 and 6 are schematic diagrams showing the different configurations of transducer array element transmitters and receivers.
Figure 4:
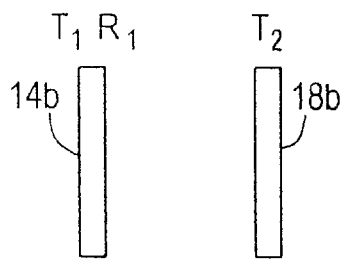
Figure 5:
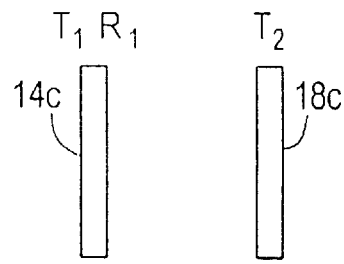

Although as shown in FIG. 2 there are two transmitter elements and one receiver element, this is not a necessary limitation of the invention. For example, as shown in FIG. 3 there may be one transmitter element 14a and two receiver elements 16a and 18a or, as in FIG. 4, there may be one element 14b which is alternately operated as a transmitter or receiver by switching circuit 20 and a second element which is always operated as a transmitter 18b. Or there may be one element 14c, FIG. 5, which is operated as a transmitter or a receiver selectively by switching circuit 20 and the second element 18c which is always operated as a receiver.

Figure 6:
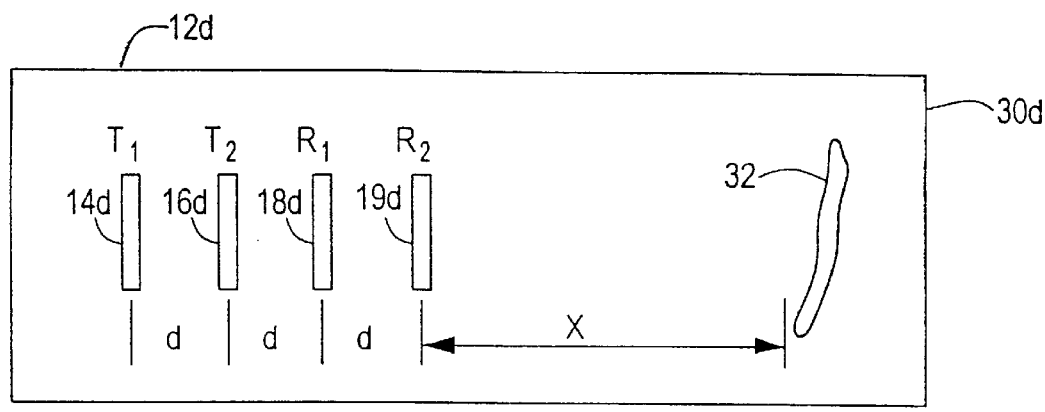

An even stronger reinforced signal can be achieved using the configuration of array elements as shown in FIG. 6 where there are two transmitters $T_1$ and $T_2$, elements 14d and 16d, and two receivers $R_1$ and $R_2$, elements 18d and 19d. These elements, as elements 14, 16 and 18 in FIG. 2, are located on a medium 30 in which the acoustic waves are to be propagated. In this particular illustration, medium 30d has a flaw 32d and the system is operating in the pulse echo mode.

Figure 7:
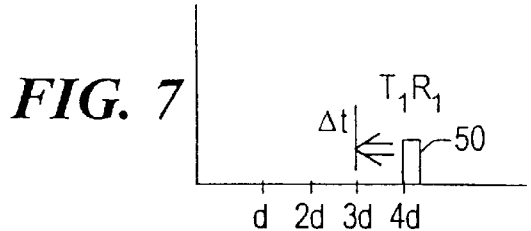
FIGS. 7–13 are graphs illustrating the waveforms and their shifting and summing in accordance with this invention.
Figure 8:
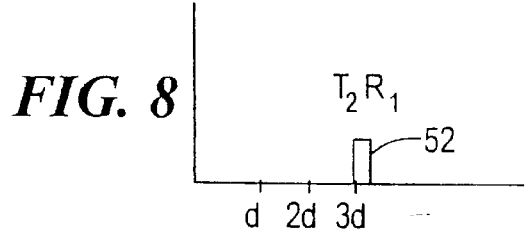
Figure 9:
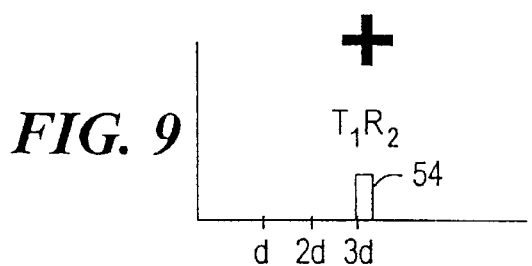
Figure 10:
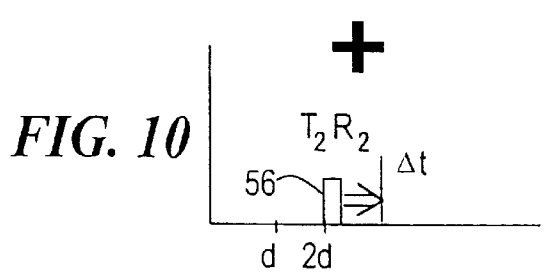
Figure 11:
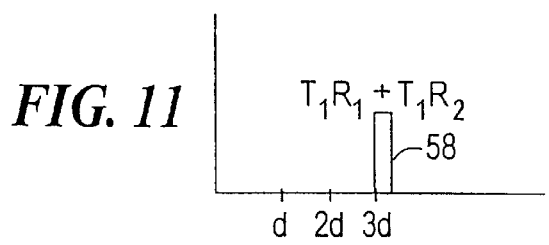
Figure 12:
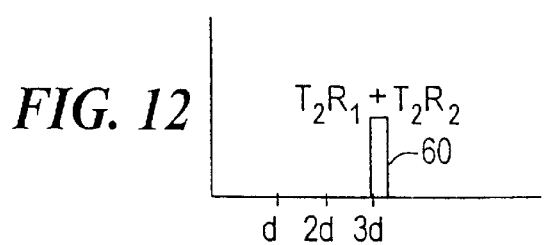
Figure 13:
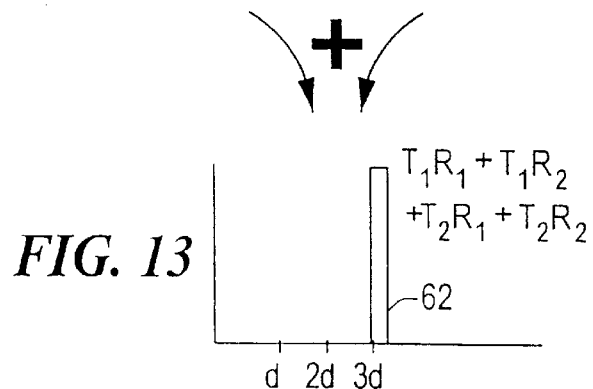

When the elements of array 12*d* are operated by the switching circuit as before, the return pulses from the activation of receiver R₁ 16*d* will appear as shown in FIGS. 7 and 8 at 50 T₁R₁ and 52 T₂R₁, respectively. Likewise, when receiver R₂ 14*d* is activated the signals received will be 54 T₁R₂ and 56 T₂R₂ in FIGS. 9 and 10, respectively. These signals 50, 52, 54 and 56 are shifted and summed as shown in FIGS. 11 and 12 where signals 50 and 54 T₁R₁ and T₁R₂ result in signal 58 T₁R₁+T₁R₂ and signals 52 T₂R₁ and 56 T₂R₂ result in signal 60 T₂R₁+T₂R₂ in FIG. 12. These two signals 58 and 60 summed in FIG. 13 to provide signal 62 which is the shifted, summed result of T₁R₁+T₁R₂+T₂R₁+T₂R₂. Assuming that T₂R₁, pulse 52, at a distance 3*d* in FIG. 8 is our reference point, T₂R₂, pulse 56 in FIG. 10, will be shifted 1*d* to the right to line up with signal 52 in FIG. 8. In contrast, the signal 50 in FIG. 7 will be shifted 1*d* to the left to the 3*d* position so it will line up with the signal 54 at the 3*d* position in FIG. 9. The shift is actually a time shift which is proportional to the value d. In accordance with the equation (2);

$$\Delta t = \frac{d}{c_p} \quad (2)$$

where d is the distance between the elements, $\Delta t$ is the time shift required and $c_p$ is the phase velocity of the selected mode in the medium.

Figure 14:
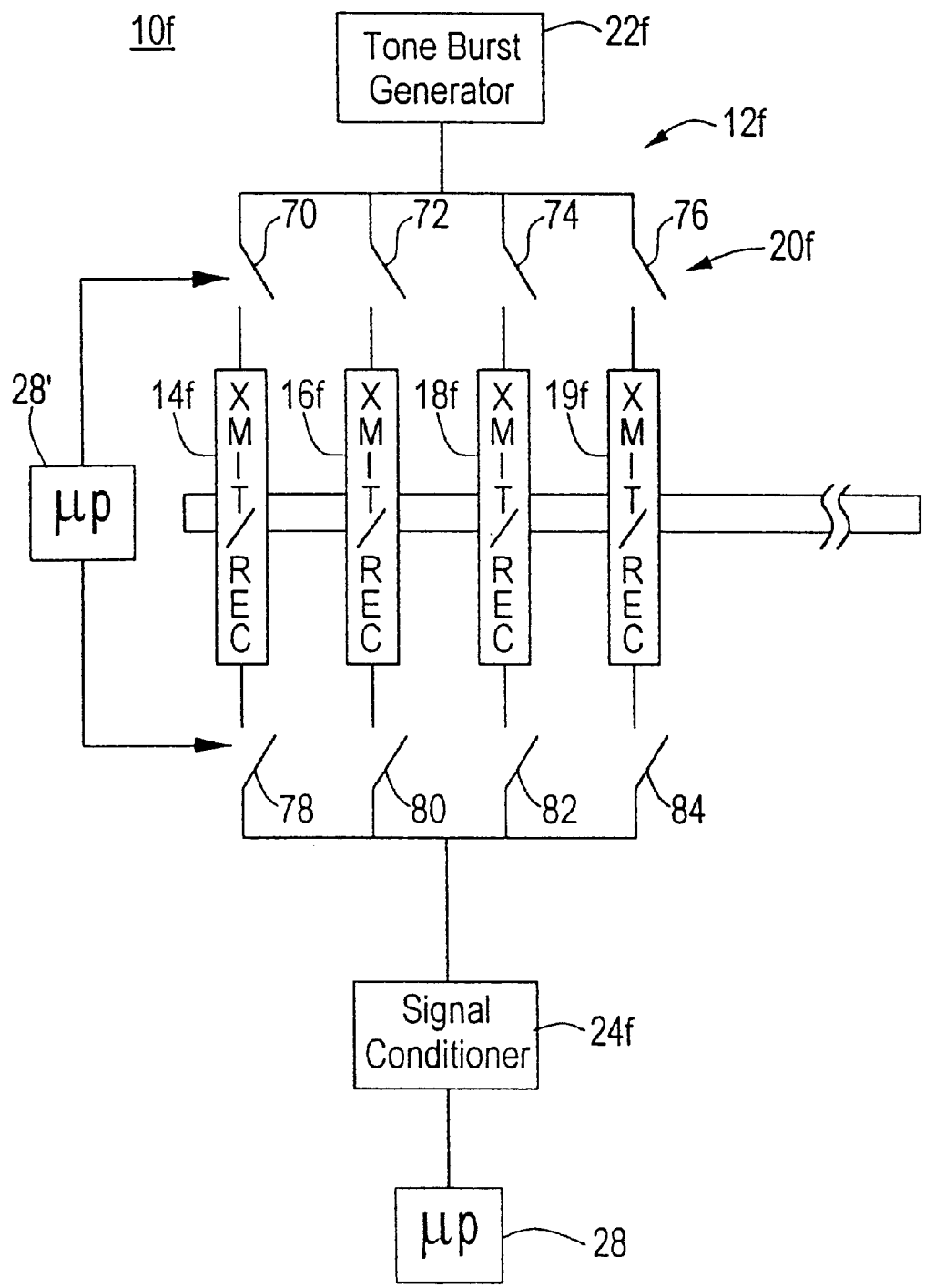
FIG. 14 is a more detailed schematic diagram of another embodiment of the invention.

In one preferred embodiment 10*f*, FIG. 14, element array 12*f* includes four transducer elements 14*f*, 16*f*, 18*f* and 19*f*, each of which may be operated as either a transmitter or a receiver by switching circuit 20*f* including a plurality of switches 70, 72, 74, 76 which interconnect the elements with a signal generator such as tone burst generator 22*f* and a second set of switches 78, 80, 82 and 84 which interconnect the elements with a signal conditioner 24*f* which can include for example a record circuit and A to D converter. Again, a microprocessor 28 may be used to time shift some of the incoming signals and the same microprocessor or another one 28' may be used to operate switching circuit 20*f*. In operation, the system drives the elements in an iterative manner so that each element operates as a transmitter while the other three individually operate as a receiver. For example, element 14*f* may be operated as a transmitter by closing switch 70 and opening switch 78. It then transmits the signal to each of elements 16*f*, 18*f* and 19*f* which are operating as receivers because switches 72, 74 and 76 are open while switches 80, 82 and 84 are closed. During the next cycle of operation element 16*f* will be operated as a transmitter by closing switch 72 and opening switch 80 and then it will transmit to each or the other elements 14*f*, 18*f* and 19*f* in turn which are operated as receivers by the fact that switches 70, 74 and 76 are open and switches 78, 82 and 84 are closed. The switches are closed sequentially, not simultaneously. That is, for example, if element 14*f* is the transmitter then switch 70 is closed and switch 78 is open, and switches 72, 74 and 76 are open but switches 80, 82 and 84 are closed sequentially: first 80 is closed then opened, then 82 is closed and opened, then 84 is closed then opened. During the period when switches 80, 82 and 84 are closed the elements 16*f*, 18*f* and 19*f* acting as receivers receive the data and forward it to signal conditioner 24*f*.

Figure 15:
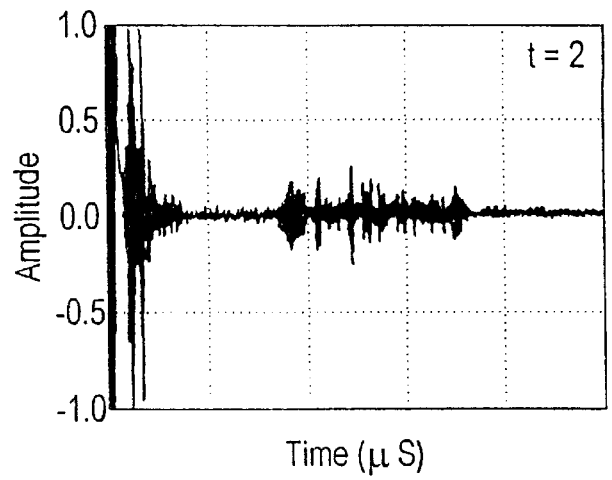
FIG. 15 is a graphical illustration of a typical untuned acoustic wave.
Figure 16:
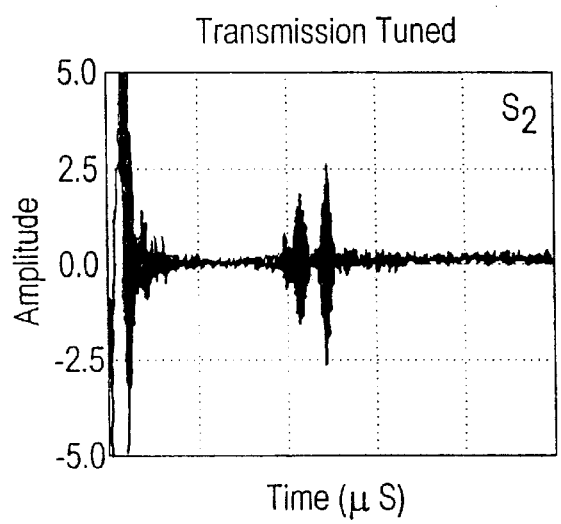
FIG. 16 is a view of a transmitter tuned acoustic wave according to this invention.
Figure 17:
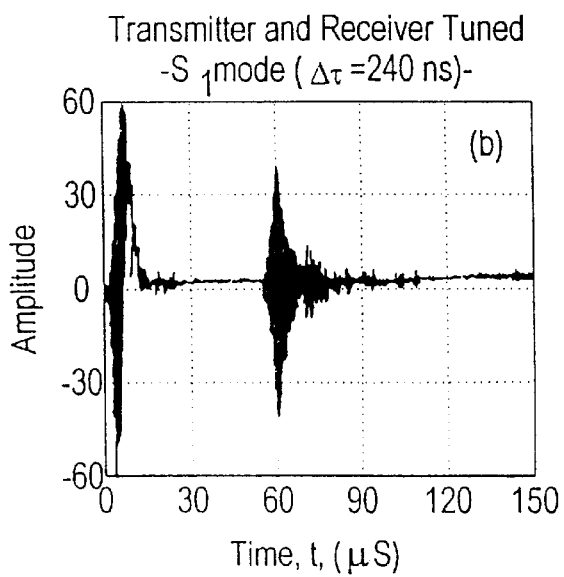
FIG. 17 is a view of a transmitter and receiver tuned acoustic wave according to this invention.

The improvement achieved with this invention can be shown by the illustrative waveforms shown in FIGS. 15, 16 and 17 where FIG. 15 shows the untuned waveform, FIG. 16 a transmission-tuned only waveform, and FIG. 17 shows a waveform which has been tuned both at transmission and reception.

Figure 1:
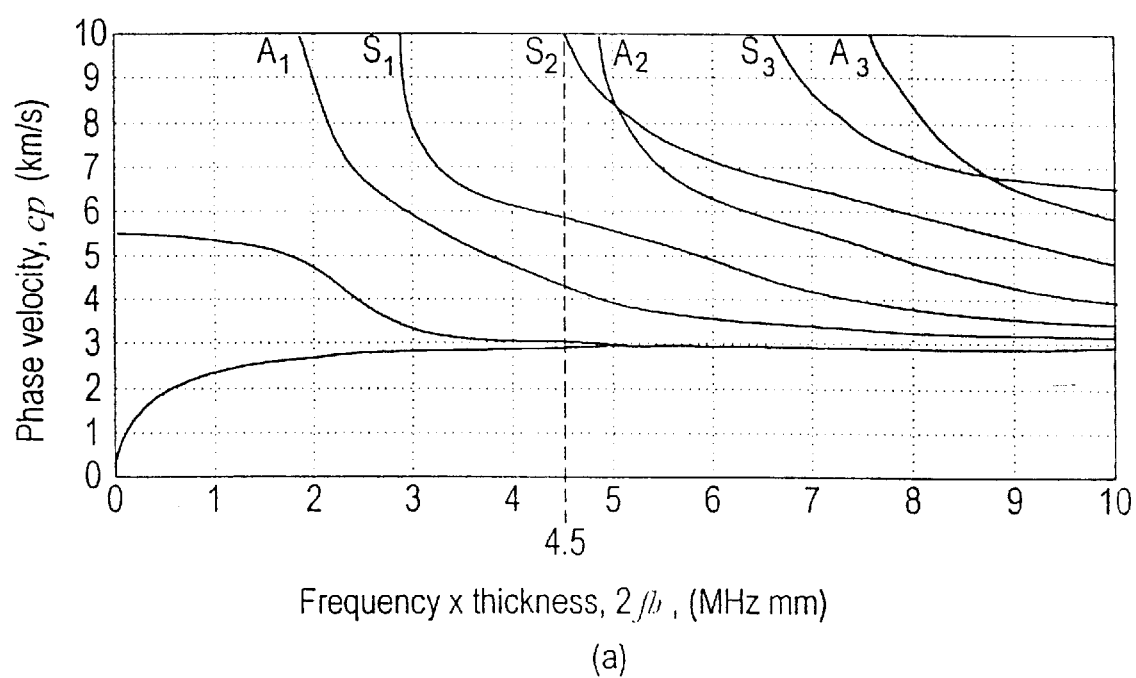
FIG. 1 is a graph showing the various wave modes for an aluminum plate of thickness 2h.

The system operates as follows. Using the graph shown in FIG. 1, the phase velocity, $c_p$, of each of the wave modes of a tone burst signal of known frequency traveling within a medium of a known thickness can be determined. Once the phase velocity of the desired wave mode is determined, the delay between the generation of signals by the transmitter can be determined in order to tune the signals to the desired wave mode. Furthermore, after the signals are generated by the transmitter elements and are reflected from a discontinuity in the medium and received by receiver, the received signals are delayed by an amount $\Delta t$, which is a function of the interelement spacing d and the phase velocity of the desired wave mode. This shifting operation is mathematically shown in the following equation for transmission tuning:

$$Sn(t) = \sum_{N=m}^{1} Smn(t - (m-1)\Delta t), n = 1, 2, 3...N \quad (3)$$

where: Sn(t)=signal received by the nth reinforced by all the transmitted signals; N=total # of elements; m=transmitter index; n=receiver index; and t=time.

The four composite signals generated from the three waves received by each of the receivers must then be summed to obtain a single synthetically tuned signal. The operations for shifting and summing the composite signals of each of the receivers is shown in the following equation:

$$S(t) = \sum_{n=N}^{1} Sn(t - (n-1)\Delta t) \quad (4)$$

At this point the waves are fully reinforced or tuned both through transmission and reception.

Real time processing of the received signals is carried out using the following equation:

$$S(t) = \sum_{n=1}^{N} \sum_{m=1}^{N} Smn\left(t - \frac{(m+n-2)d}{c_p}\right) \quad (5)$$

At the end of the acquisition, a fully synthesized pseudo pulse-echo signal is readily available for display and analysis. Once the fully synthesized signal is determined, the elapsed time between the initial transmission and the synthetic signal is used to determine the location of the discontinuity in the medium 30.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

Other embodiments will occur to those skilled in the art and are within the following claims:

What is claimed is:

1. A synthetic phase tuned multi-mode acoustic guided wave system comprising:
   a plurality of spaced transducer elements;
   a switching device for activating at least one of said elements as a receiver or a transmitter and at least two of said elements as transmitters or receivers, respectively; and a control device for sequentially exciting each of said transmitter elements for creating a train of acoustic guided waves which includes a selected mode, and for shifting the acoustic guided waves of the selected mode sensed by said receivers by a period which is a function of the phase velocity of the selected mode and summing them to reinforce the selected mode.

2. A synthetic phase tuned multi-mode acoustic guided wave system comprising:

a plurality of spaced transducer elements;

a switching device for activating one of said elements as a receiver and at least two of said elements as transmitters; and a control device for sequentially exciting each of said transmitter elements for creating a train of acoustic guided waves which includes a selected mode, and for shifting the acoustic guided waves of the selected mode sensed by said receivers by a period which is a function of the phase velocity of the selected mode and summing them to reinforce the selected mode.

3. A synthetic phase tuned multi-mode acoustic guided wave system comprising:

a plurality of spaced transducer elements;

a switching device for activating at least two of said elements as a receiver and at least one of said elements as a transmitter; and a control device for sequentially exciting each of said transmitter elements for creating a train of acoustic guided waves which includes a selected mode, and for shifting the acoustic guided waves of the selected mode sensed by said receivers by a period which is a function of the phase velocity of the selected mode and summing them to reinforce the selected mode.

4. A method for synthetic phase tuning of acoustic guided waves comprising:

activating at least one of a plurality of elements as a receiver or a transmitter and at least two of said elements as transmitters or receivers, respectively; and sequentially exciting each of said transmitter elements for creating a train of acoustic guided waves which includes a selected mode, and shifting the acoustic guided waves of the selected mode sensed by said receivers by a period which is a function of the phase velocity of the selected mode and summing them to reinforce the selected mode.

5. A method for synthetic phase tuning of acoustic guided waves comprising:

activating at least one of a plurality of elements as a receiver and at least two of said elements as transmitters; and a control device for sequentially exciting each of said transmitter elements for creating a train of acoustic guided waves which includes a selected mode, and shifting the acoustic guided waves of the selected mode sensed by said receivers by a period which is a function of the phase velocity of the selected mode and summing them to reinforce the selected mode.

6. A method for synthetic phase tuning of acoustic guided waves comprising:

activating at least two of a plurality of elements as a receiver and at least one of said elements as a transmitter; and a control device for sequentially exciting each of said transmitter elements for creating a train of acoustic guided waves which includes a selected mode, and shifting the acoustic guided waves of the selected mode sensed by said receivers by a period which is a function of the phase velocity of the selected mode and summing them to reinforce the selected mode.

* * * * *